United States Patent
Zhu

(10) Patent No.: US 9,655,528 B2
(45) Date of Patent: May 23, 2017

(54) SYSTEMS AND METHODS FOR DETECTING CEREBROSPINAL-FLUID PULSATION USING AN IMPLANTABLE ELECTRICAL STIMULATION DEVICE

(71) Applicant: BOSTON SCIENTIFIC NEUROMODULATION CORPORATION, Valencia, CA (US)

(72) Inventor: Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 355 days.

(21) Appl. No.: 14/330,286

(22) Filed: Jul. 14, 2014

(65) Prior Publication Data

US 2015/0018634 A1    Jan. 15, 2015

Related U.S. Application Data

(60) Provisional application No. 61/846,481, filed on Jul. 15, 2013.

(51) Int. Cl.
*A61N 1/08* (2006.01)
*A61B 5/0205* (2006.01)
(Continued)

(52) U.S. Cl.
CPC .......... *A61B 5/0205* (2013.01); *A61B 5/4058* (2013.01); *A61B 5/6868* (2013.01);
(Continued)

(58) Field of Classification Search
CPC ... A61B 5/0205; A61B 5/4058; A61B 5/6868; A61B 5/7278; A61B 5/026; A61B 5/0059; A61N 1/0551; A61N 1/36135
(Continued)

(56) References Cited

U.S. PATENT DOCUMENTS 6,181,969 B1    1/2001 Gord
6,516,227 B1    2/2003 Meadows et al.
(Continued)

OTHER PUBLICATIONS

Linninger, Andreas, et al. "A mathematical model of blood, cerebrospinal fluid, and brain dynamics." Jun. 13, 2008. Mathematical Biology. vol. 59. pp. 729-759.*

(Continued)

*Primary Examiner* — Michael Carey
(74) *Attorney, Agent, or Firm* — Lowe Graham Jones PLLC; Bruce E. Black

(57) ABSTRACT

An electrical stimulation lead assembly includes a lead body having a distal end portion, a proximal end portion, and a longitudinal length. Electrodes are disposed along the distal end portion of the lead body; terminals disposed along the proximal end portion of the lead body; and stimulation conductors couple the terminals to the electrodes. A cerebrospinal-fluid-pulsation detection assembly includes a sensor disposed along the distal end portion of the lead body. The sensor detects pulses of cerebrospinal fluid within a subarachnoid space of a patient and transforms the detected cerebrospinal-fluid pulses into sensor signals. A sensor processor receives the sensor signals from the sensor, processes the received sensor signals to cerebrospinal-fluid pulsation data ("CSF-pulsation data"), and estimates a patient blood-flow condition based on the CSF-pulsation data. A sensor control pathway couples the sensor to the sensor processor.

20 Claims, 12 Drawing Sheets

(51) Int. Cl.
*A61B 5/00* (2006.01)
*A61N 1/05* (2006.01)
*A61N 1/36* (2006.01)
*A61B 5/026* (2006.01)

(52) U.S. Cl.
CPC .......... *A61B 5/7278* (2013.01); *A61N 1/0551* (2013.01); *A61N 1/36135* (2013.01); *A61B 5/0059* (2013.01); *A61B 5/026* (2013.01)

(58) Field of Classification Search
USPC .......................... 607/62, 117; 600/587, 594
See application file for complete search history.

(56) References Cited

U.S. PATENT DOCUMENTS

| | | |
|---|---|---|
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 2007/0150036 A1 | 6/2007 | Anderson |
| 2007/0265664 A1* | 11/2007 | Gerber ............... A61N 1/36071 607/2 |
| 2009/0187222 A1 | 7/2009 | Barker |
| 2009/0276021 A1 | 11/2009 | Meadows et al. |
| 2010/0057163 A1 | 3/2010 | Moffitt et al. |
| 2010/0076535 A1 | 3/2010 | Pianca et al. |
| 2010/0268298 A1 | 10/2010 | Moffitt et al. |
| 2010/0331934 A1* | 12/2010 | McDonald ............... A61N 1/05 607/116 |
| 2011/0004267 A1 | 1/2011 | Meadows |
| 2011/0005069 A1 | 1/2011 | Pianca |
| 2011/0054353 A1* | 3/2011 | Hulvershorn .......... A61B 5/032 600/587 |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0014580 A1 | 1/2012 | Blum et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |

OTHER PUBLICATIONS

Dynamics of the Cerebrospinal Fluid and the Spinal Dura Matter, A. N. Martins, J. K. Wiley and P. W. Myers. J Neurol Neurosurg Psychiatry 1972 35: 468-473.

Cerebrospinal Fluid Pulsation Amplitude and Its Quantitative Relationship to Cerebral Blood Flow Pulsations: A Phase-Contrast MR Flow Imaging Study, R. A. Bhadelia, A. R. Bogdan, R. F. Kaplan and S. M. Wolpert, Neuroradiology 1997 39: 258-264.

Influence of Systemic and Cerebral Vascular Factors on the Cerebrospinal Fluid Pulse Waves, J. Hamer, E. Alberti, S. Hoyer and K. Wiedemann, J. Neurosurg. 1977 46: 36-45.

From Cerebrospinal Fluid Pulsation to Noninvasive Intracranial Compliance and Pressure measured by MRI Flow Studies, N. Alperin, M. Mazda, T. Lichtor and S. H. Lee, Current Medical Imaging Reviews 2006 2: 117-129.

Holsheimer, J. et al. "MR Assessment of the Normal Position of the Spinal Cord in the Spinal Canal." AJNR 15:951-959. 1994.

* cited by examiner

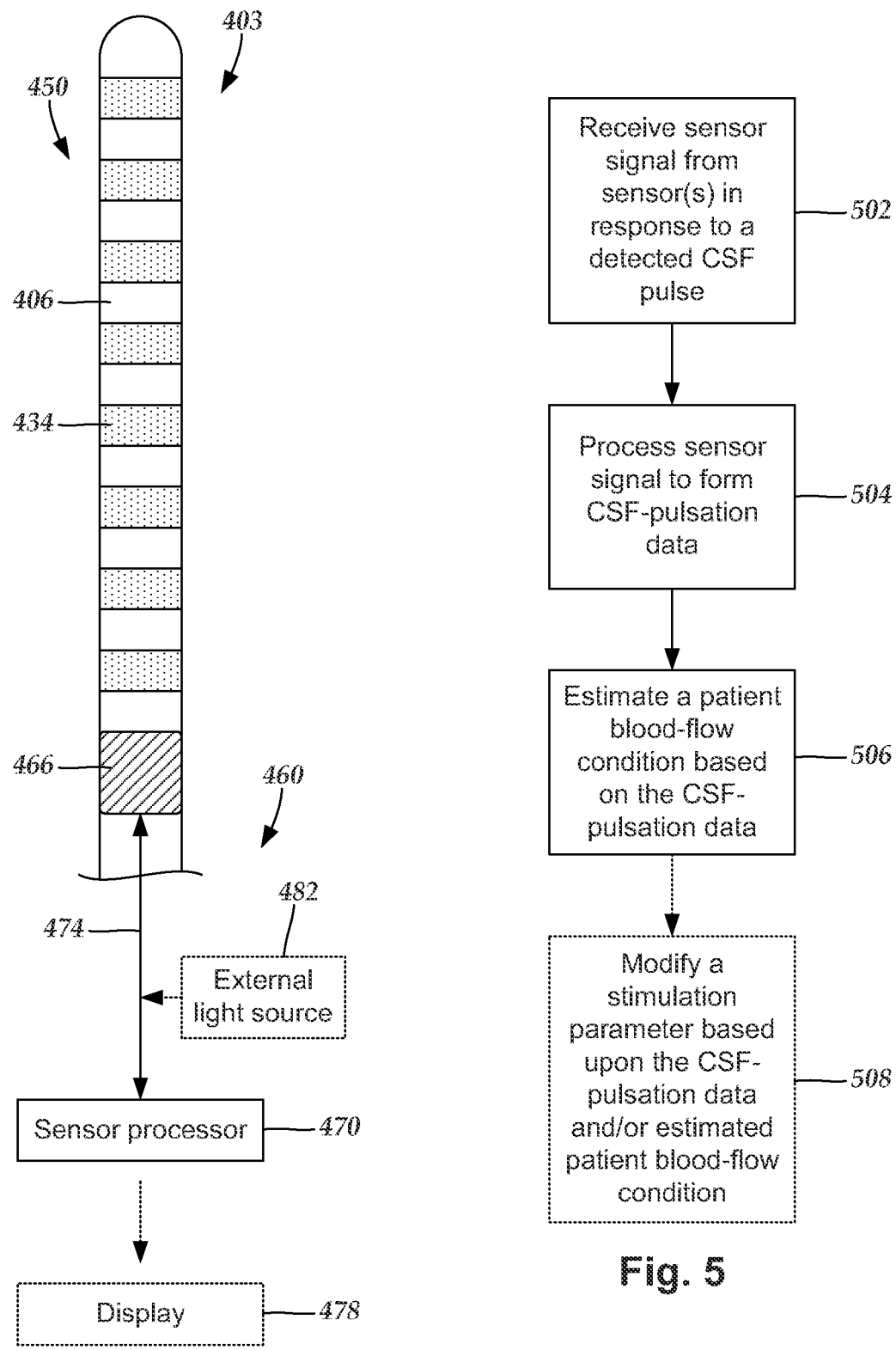

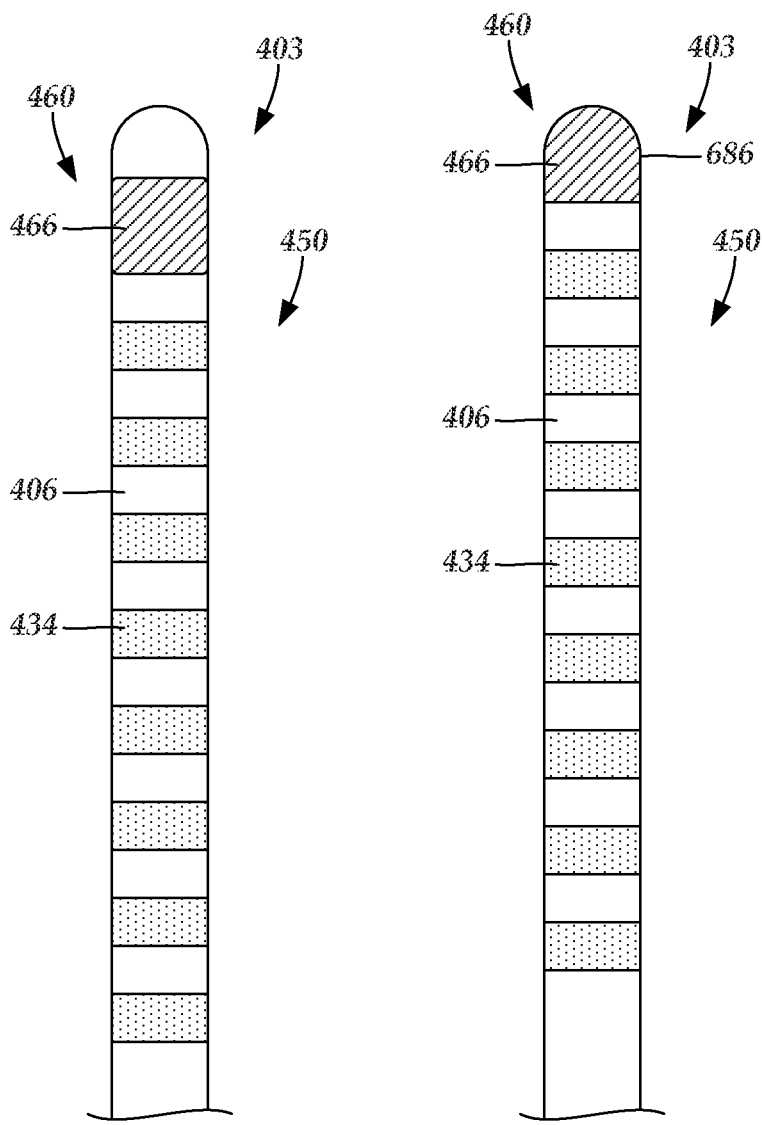

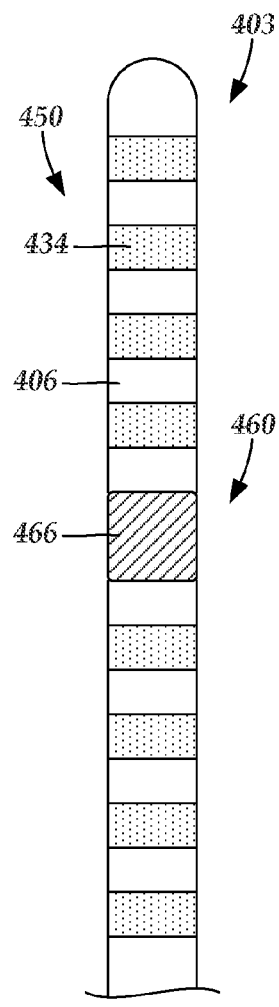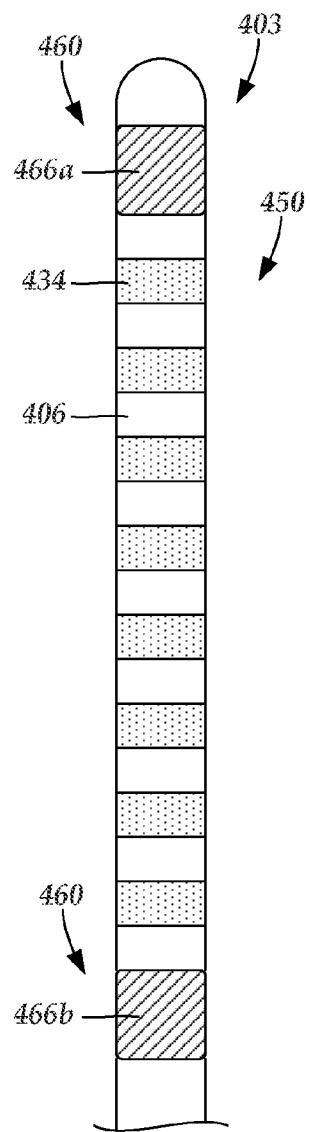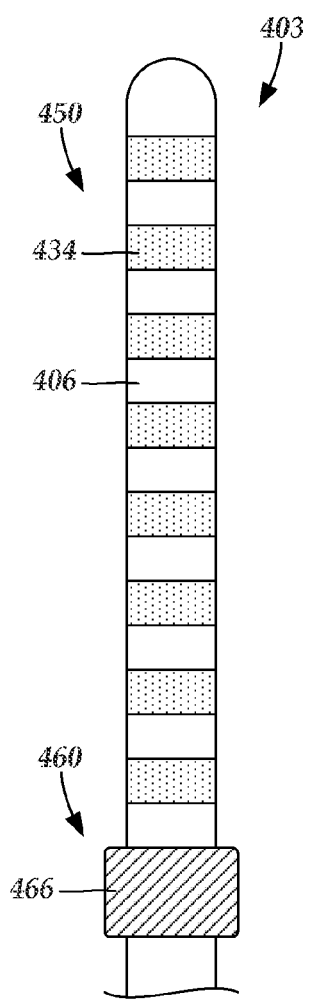
Fig. 6C
Fig. 6D
Fig. 6E

SYSTEMS AND METHODS FOR DETECTING CEREBROSPINAL-FLUID PULSATION USING AN IMPLANTABLE ELECTRICAL STIMULATION DEVICE

CROSS-REFERENCE TO RELATED APPLICATIONS

This application claims the benefit under 35 U.S.C. §119 (e) of U.S. Provisional Patent Application Ser. No. 61/846,481, filed Jul. 15, 2013, which is incorporated herein by reference.

FIELD

The present invention is directed to the area of implantable electrical stimulation systems and methods of making and using the systems. The present invention is also directed to implantable electrical stimulation systems having leads capable of detecting pulsation of cerebrospinal fluid within a patient in addition to providing stimulation, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical signals that are delivered by the electrodes to body tissue.

BRIEF SUMMARY

In one embodiment, an electrical stimulation lead assembly includes at least one lead body having a distal end portion, a proximal end portion, and a longitudinal length. Electrodes are disposed along the distal end portion of the at least one lead body; terminals disposed along the proximal end portion of the at least one lead body; and stimulation conductors couple the terminals to the electrodes. A cerebrospinal-fluid-pulsation detection assembly includes at least one sensor disposed along the distal end portion of the lead body. The at least one sensor is configured and arranged for detecting pulses of cerebrospinal fluid within a subarachnoid space of a patient and transforming the detected cerebrospinal-fluid pulses into sensor signals. A sensor processor receives the sensor signals from the at least one sensor, processes the received sensor signals to cerebrospinal-fluid pulsation data ("CSF-pulsation data"), and estimates at least one patient blood-flow condition based on the CSF-pulsation data. At least one sensor control pathway couples the at least one sensor to the sensor processor.

In another embodiment, a non-transitory computer-readable medium has processor-executable instructions for reading data from at least one sensor disposed along a distal end portion of an electrical stimulation lead of an electrical stimulation system. The processor-executable instructions, when installed onto a device, enable the device to perform actions, including: receiving a sensor signal from the at least one sensor; processing the received sensor signal to generate cerebrospinal-fluid pulsation data; and estimating at least one patient blood-flow condition based on the CSF-pulsation data.

In yet another embodiment, a lead-based stimulator includes at least one stimulator and at least one sensor disposed along an electrical stimulation lead insertable into a patient. The stimulator is configured and arranged to stimulate patient tissue. The at least one sensor is configured and arranged for detecting cerebrospinal-fluid-pulsation. The at least one stimulator and the at least one sensor are each coupled to a control module. A processor is in communication with the control module. The processor executes processor-readable instructions that enable actions, including: receiving a sensor signal from the at least one sensor, processing the received sensor signal to generate cerebrospinal-fluid pulsation data, and estimating at least one patient blood-flow condition based on the CSF-pulsation data.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4 is a schematic view of one embodiment of a distal end portion of an electrical stimulation lead and a cerebrospinal-fluid-pulsation detection assembly that includes a sensor for detecting cerebrospinal-fluid-pulsation and a sensor processor, the sensor disposed along the distal end portion of the electrical stimulation lead, according to the invention;

FIG. 5 is a flow diagram of one exemplary embodiment of a cerebrospinal-fluid-pulsation detection procedure between a sensor and a sensor processor of a lead-based stimulation system, according to the invention;

FIG. 6A is a schematic side view of one embodiment of a sensor of the cerebrospinal-fluid-pulsation detection assembly of FIG. 4 disposed along a distal end portion of the lead of FIG. 4, the sensor disposed distally to electrodes also disposed along the distal end portion of the lead, according to the invention;

FIG. 6B is a schematic side view of one embodiment of a sensor of the cerebrospinal-fluid-pulsation detection assembly of FIG. 4 disposed along a distal end portion of the lead of FIG. 4, the sensor disposed at a distal tip of the lead, according to the invention;

FIG. 6C is a schematic side view of one embodiment of a sensor of the cerebrospinal-fluid-pulsation detection assembly of FIG. 4 disposed along a distal end portion of the lead of FIG. 4, the sensor disposed between two electrodes axially-spaced apart from one another along the distal end portion of the lead, according to the invention;

FIG. 6D is a schematic side view of one embodiment of multiple sensors of the cerebrospinal-fluid-pulsation detection assembly of FIG. 4 disposed along a distal end portion of the lead of FIG. 4, with a first sensor disposed distally to electrodes also disposed along the distal end portion of the lead and a second sensor disposed proximally to the electrodes, according to the invention;

FIG. 6E is a schematic side view of one embodiment of a sensor of the cerebrospinal-fluid-pulsation detection assembly of FIG. 4 disposed along a distal end portion of the lead of FIG. 4, the sensor having a diameter that is larger than a diameter of the lead, according to the invention;

DETAILED DESCRIPTION

Figure 1:
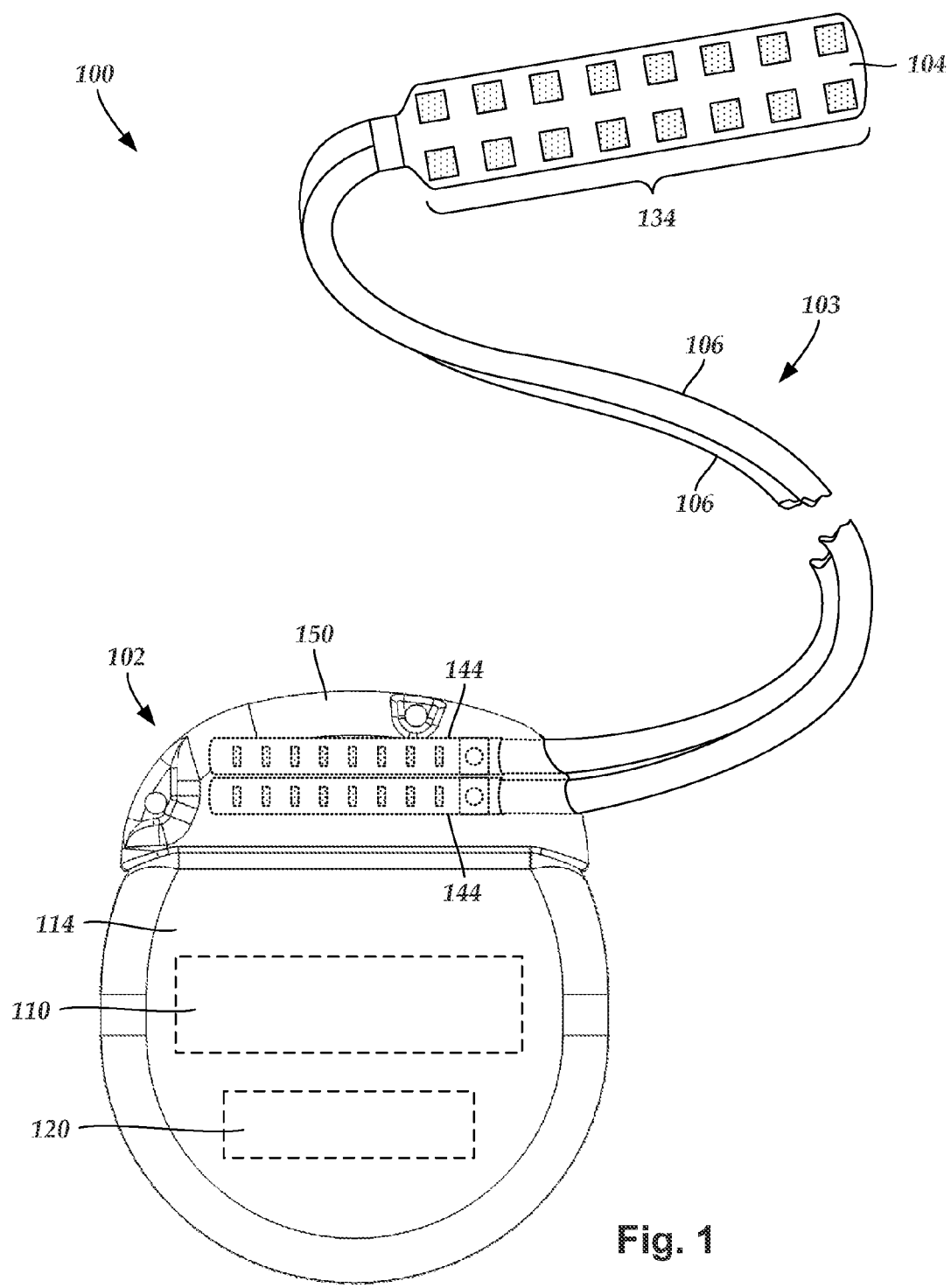
FIG. 1 is a schematic view of one embodiment of an electrical stimulation system that includes a paddle lead electrically coupled to a control module, according to the invention.

The present invention is directed to the area of implantable electrical stimulation systems and methods of making and using the systems. The present invention is also directed to implantable electrical stimulation systems having leads capable of detecting pulsation of cerebrospinal fluid within a patient in addition to providing stimulation, as well as methods of making and using the leads and electrical stimulation systems.

The methods, systems, and devices described herein may be embodied in many different forms and should not be construed as limited to the embodiments set forth herein. Accordingly, the methods, systems, and devices described herein may take the form of an entirely hardware embodiment, an entirely software embodiment or an embodiment combining software and hardware aspects. The methods described herein can be performed using any type of computing device, such as a computer, that includes a processor or any combination of computing devices where each device performs at least part of the process.

Suitable computing devices typically include mass memory and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Methods of communication between devices or components of a system can include both wired and wireless (e.g., RF, optical, or infrared) communications methods and such methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
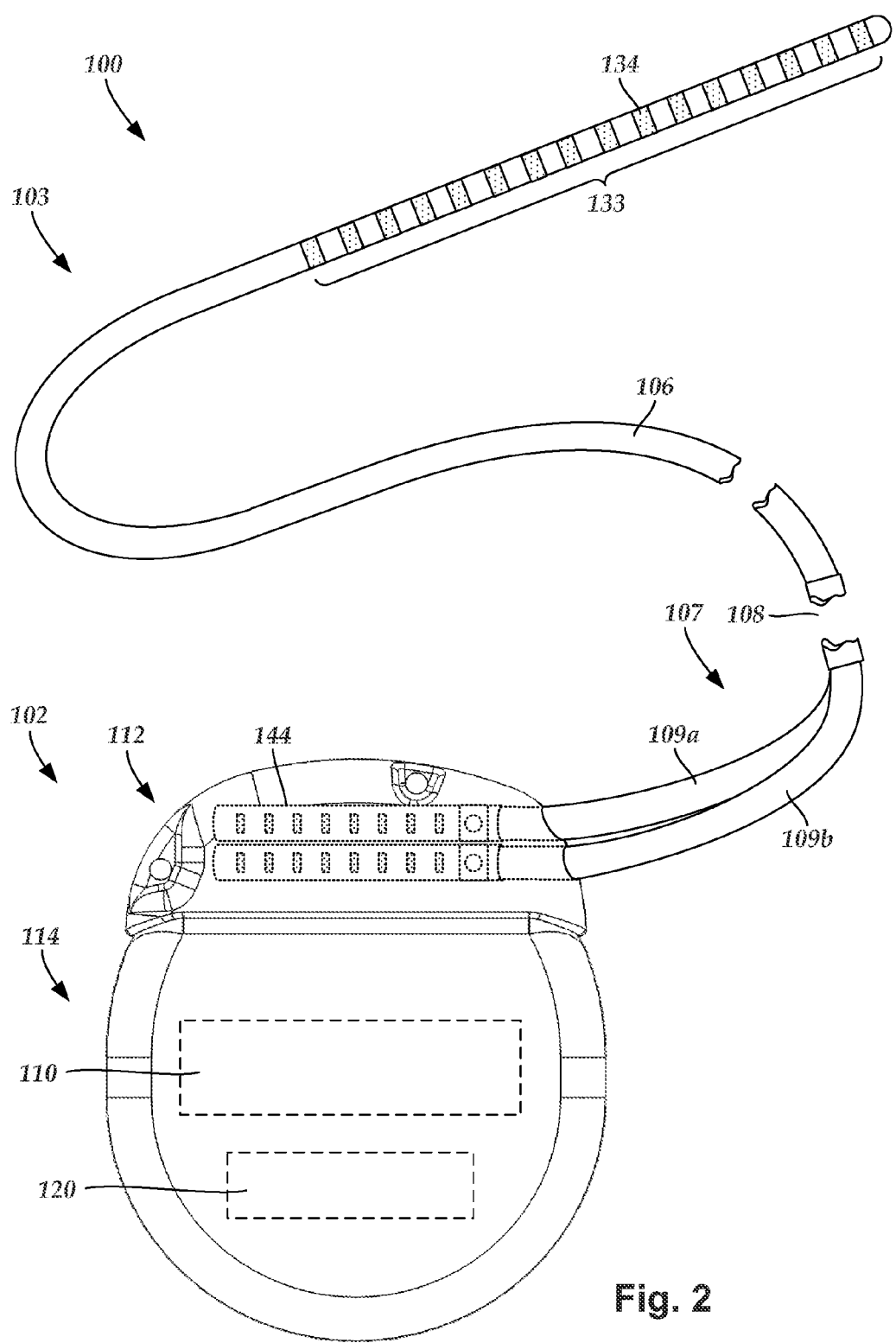
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
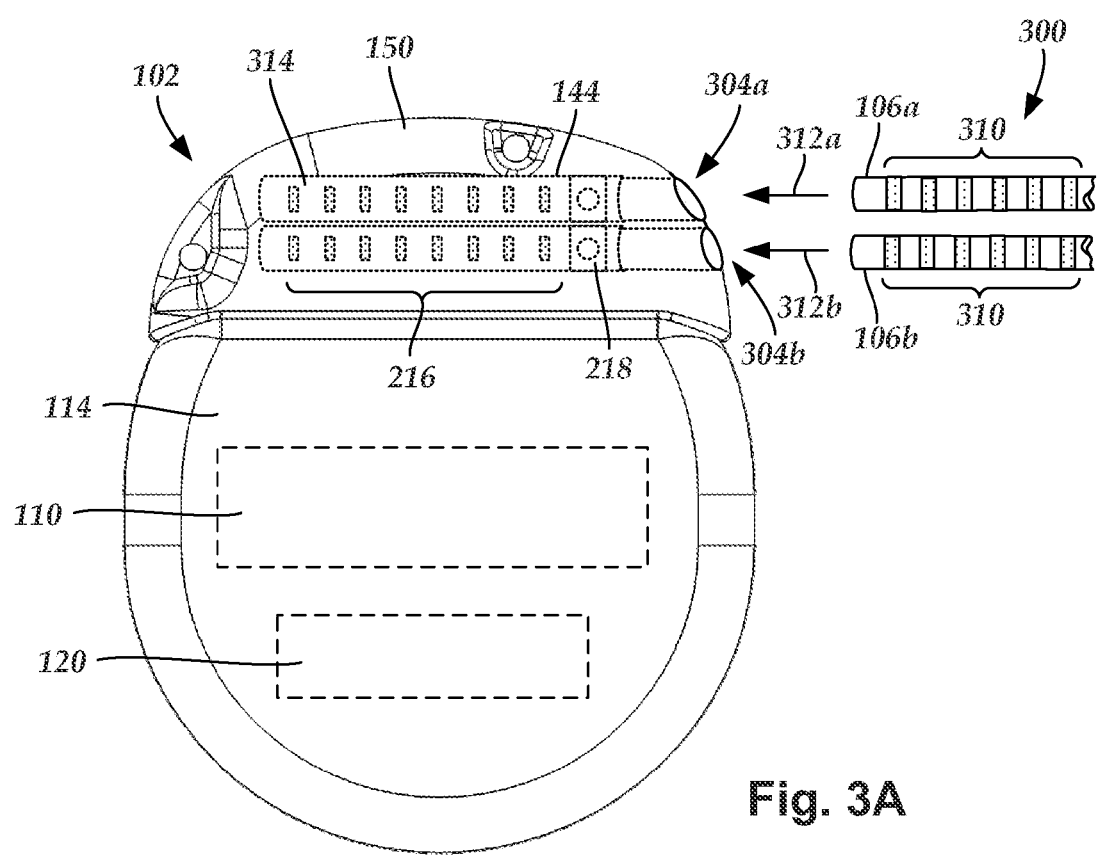
FIG. 3A is a schematic view of one embodiment of the control module of FIG. 1 configured and arranged to electrically couple to an elongated device, according to the invention.
Figure 3B:
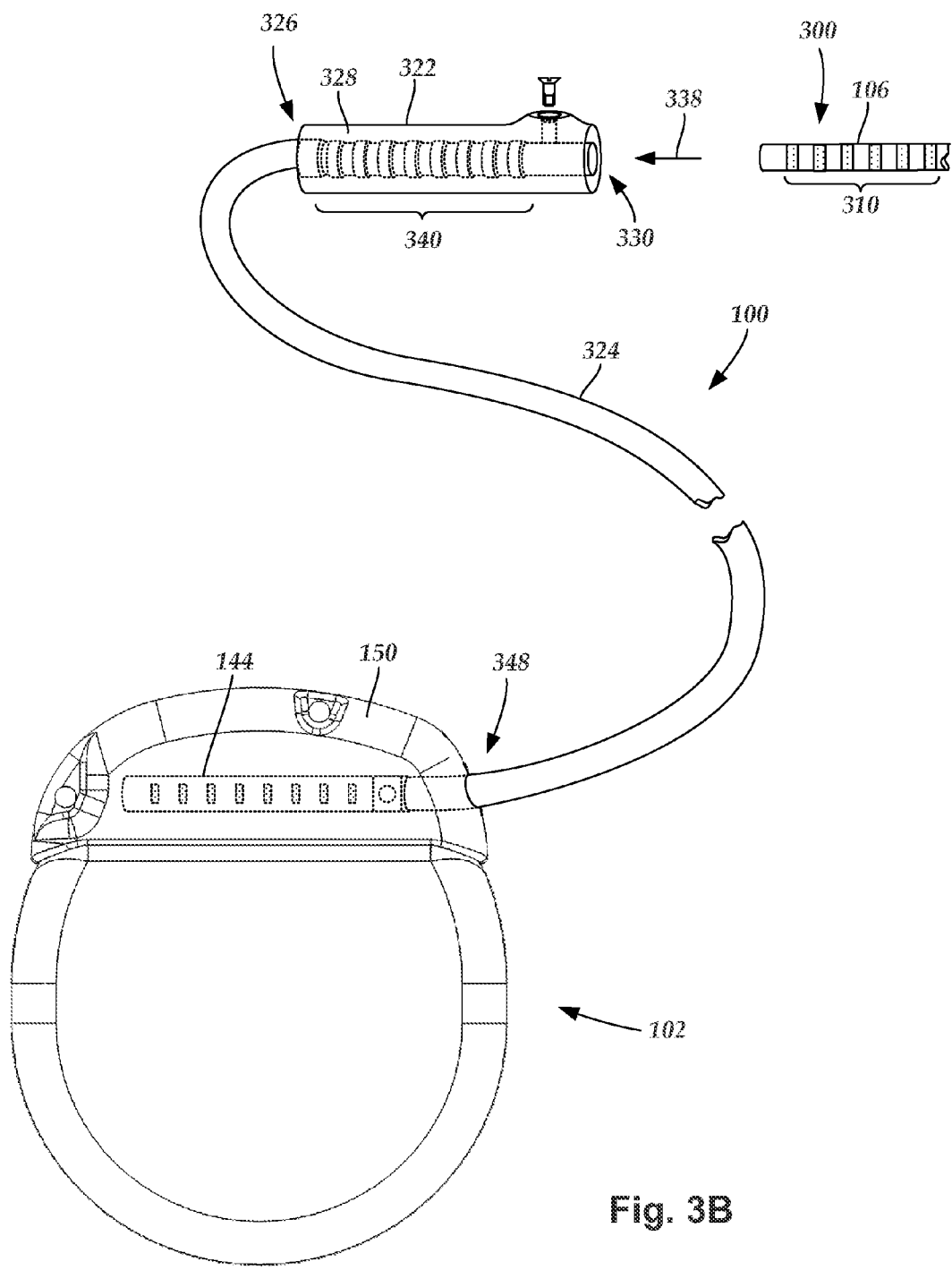
FIG. 3B is a schematic view of one embodiment of a lead extension configured and arranged to electrically couple the elongated device of FIG. 2 to the control module of FIG. 1, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 240 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Turning to FIG. 4A, two possible target stimulation locations are the brain and spinal cord of a patient. The brain and spinal cord are both surrounded by meninges (dura mater, arachnoid mater, and pia mater). Cerebrospinal fluid ("CSF") is disposed in a subarachnoid space, between the arachnoid mater and the pia mater. During the cardiac cycle, the flow of blood (distribution and/or volume) caused by normal operation of the heart causes a corresponding circulation of CSF within the subarachnoid space. At least some research suggests that the subarachnoid space is often not filled to capacity and receives additional CSF, or removes excess CSF, via the foramen magnum, according to a pressure gradient caused, at least in part, by the cardiac cycle.

At least some studies have measured the flow of CSF and suggest a correlation between the amplitude and rate of CSF pulses and both arterial and venous blood flow. It is possible to measure intracranial compliance and pressure during CSF flow. Measuring intracranial compliance and pressure may be used to estimate one or more patient blood-flow conditions including, for example, heart beat rate, cerebral arterial and/or venous blood flow dynamics, as well as patient activity status. For example, an increasing CSF pulsation rate may indicate an increasing heart beat rate. As another example, increasing CSF pulsation amplitude may indicate increasing cerebral arterial blood flow. When taken together, an increasing heart beat rate and increasing cerebral arterial blood flow may indicate an increasing activity status.

Additionally, estimated patient blood-flow conditions may include patient posture. At least one study has suggested that when a patient is in a supine position the volume of CSF blood flow is significantly different than when the patient is in an upright position. Thus, if the flow volume change is reflected in the CSF pulsation, detecting the difference in CSF pulsation as a result of different postures may be used to estimate patient posture (e.g., whether a patient is standing or in a supine position).

As mentioned above, at least some leads of electrical stimulation systems are implanted within the brain or epidural space of a patient and used to stimulate nearby tissue. As herein described, leads can be adapted such that, in addition to providing electrical stimulation to patient tissue (e.g., in the brain or spinal cord), the leads can also detect CSF pulsation using a CSF-pulsation detection assembly. In at least some embodiments, the leads stimulate patient tissue and detect CSF pulsation simultaneously.

The detected CSF pulsation can, optionally, be used for estimating patient blood-flow condition including, for example, the patient's heart beat rate, cerebral arterial and/or venous blood flow dynamics, activity status, posture, or the like or combinations thereof. In at least some embodiments, the detected CSF pulsation is processed and used to adapt one or more stimulation parameters (e.g., the timing, frequency, strength, duration, waveform, or the like or combinations thereof of the signals) of the implanted electrical stimulation system.

The CSF-pulsation detection assembly includes one or more sensors for detecting CSF pulsation and transforming the detected CSF pulsation into a sensor signal. The one or more sensors are coupled to a processor for processing the transformed sensor signal. The processor can be disposed in any suitable location. In at least some embodiments, the processor is a stand-alone device that is external to the lead. In at least some embodiments, the processor is external to the patient. In at least some embodiments, the processor is disposed in the control module. In at least some embodiments, the processor is the same processor (see e.g., 804 in FIG. 8) used to generate the signals used for stimulation.

The one or more sensors can be disposed at any suitable location along the lead. It may be advantageous to dispose at least one of the one or more sensors along the distal end portion of the lead. In the case of, for example, spinal cord stimulation the distal end portion of the lead is typically implanted into the patient's epidural space, which is disposed directly over the meninges, while the remaining portions of the lead may be disposed external to the epidural space. The dura mater has an elastic quality, due to an abundance of veins and fat. In at least some embodiments, the elastic quality of the dura mater may be utilized to facilitate detection of CSF pulses from the epidural space.

FIG. 4 illustrates schematically, in side view, one embodiment of a distal end portion 450 of a lead body 406 of a lead 403. Electrodes, such as electrode 434, are disposed along the distal end portion 450 of the lead body 406. FIG. 4 also illustrates schematically a CSF-pulsation detection assembly 460 that includes a sensor 466 coupled to a sensor processor 470 via a sensor control pathway 474. The sensor 466 is disposed along the distal end portion 450 of the lead body 406. The sensor control pathway 474 can be either a physical connection (e.g., one or more conductors, conduits, or the like or combinations thereof) or a wireless connection.

The sensor 466 detects CSF pulsation within the patient in proximity to the lead 403. The detected CSF pulsations are transformed into sensor signals that are transmitted to the sensor processor 470 via the sensor control pathway 474. The sensor signals can be any suitable type of signal including, for example, electrical signals, optical signals, or the like or combinations thereof.

The transmitted sensor signals include information related to the detected CSF pulsation (e.g., the amplitudes of one or more pulses, the durations of one more pulses, the frequencies of repeated pulsing, or the like or combinations thereof). The sensor processor 470 processes the received sensor signals to form CSF-pulsation data.

Optionally, the CSF-pulsation data is used to estimate one or more patient blood-flow conditions, such as heart beat rate, cerebral arterial and/or venous blood flow dynamics, as well as patient activity status, body position, or both. The CSF-pulsation detection assembly 460 may also include a display 478 for displaying the one or more patient blood-flow conditions. The display 478 is typically disposed external to the patient and coupled to the sensor processor 470 via a wireless connection.

In at least some embodiments, one or more stimulation parameters (e.g., the timing, frequency, strength, duration, waveform, or the like, of the signals) may be adapted over time based on the collected CSF-pulsation data. For example, stimulation may be changed when the CSF-pulsation data (or the estimated blood-flow conditions) suggests that the patient is engaged in heightened physical activity (e.g., exercising, or the like), or oriented in a supine position (e.g., sleeping, or the like).

As shown in FIG. 4, and as described in further detail below with reference to FIGS. 6A-7H, the one or more sensors used for detecting CSF pulsation within the patient are disposed along the distal end portion of the lead. Any sensor suitable for implantation and for detecting CSF pulsation may be used including, for example, optical sensors (e.g., electro-optical sensors, such as photoelectric sensors, pulse oximeters, and the like or combinations thereof), piezoelectric sensors, strain gauges (e.g., fiberoptic strain gauges, semiconductor strain gauges, or the like or combinations thereof), level sensors (e.g., pneumatic sensors, or the like).

Optical sensors typically include a light source and a photo-detector for detecting light received from the light source. In at least some embodiments, the light source is disposed along the distal end portion of the lead body. Any light source suitable for disposing along the distal end portion of the lead body may be used including, for example, one or more light-emitting diodes, laser diodes, or the like.

In at least some embodiments, the light source is disposed external to the lead body (i.e., an external light source 482). Light from the external light source 482 can be provided to the sensor 466 via the one or more sensor control pathways 474 configured as one or more optical transport media (e.g., optical fibers, light pipes, light guides, light tubes, or the like). The external light source 482 can, optionally, be disposed in the control module, or can be disposed external to the control module.

As mentioned above, the sensor control pathways 470, in some embodiments, include one or more optical transport media in addition to media used for transmitting sensor signals from the one or more sensors 466 to the sensor processor 470. Alternately or additionally, the one or more sensor control pathways 474 can be used to provide energy to power the one or more sensors 466. In at least some embodiments, the power is supplied via the control module (see e.g., 120 in FIGS. 1 and 812 in FIG. 8). In at least some other embodiments, the power is supplied by a power source external to the control module.

FIG. 5 is a flow diagram of one exemplary embodiment of a cerebrospinal-fluid-pulsation detection procedure between the sensor processor 470 and the one or more sensors 466 of the lead-based stimulation system 460. In block 502, the sensor processor 470 receives a sensor signal from the one or more sensors 466, the sensor signal transformed from a CSF pulse detected from the one or more sensors 466. In block 504, the received sensor signal is processed to form CSF-pulsation data. In block 506, a patient blood-flow condition is estimated using the CSF-pulsation data. Optionally, in block 508 a stimulation parameter of the electrical stimulation system is modified based upon the CSF-pulsation data or the estimated patient blood-flow condition.

Turning to FIG. 6A, the one or more sensors can be disposed at any suitable location along the distal end portion of the lead body. In FIG. 5, a single sensor 466 is shown disposed along the distal end portion 450 of the lead 403 such that the sensor 466 is disposed proximal to all of the electrodes 434. FIGS. 6A-7H illustrate several alternate embodiments with the one or more sensors disposed at different locations along the distal end portion of the lead.

FIG. 6A schematically illustrates, in side view, one embodiment of the electrodes 434 and the sensor 466 of the CSF-pulsation detection assembly 460 disposed along the distal end portion 450 of the lead 403. In FIG. 6A, the sensor 466 is shown disposed distal to all of the electrodes 434.

FIG. 6B schematically illustrates, in side view, another embodiment of the electrodes 434 and the sensor 466 of the CSF-pulsation detection assembly 460 disposed along the distal end portion 450 of the lead 403. In FIG. 6B, the sensor 466 is shown disposed at a distal tip 686 of the lead 403.

FIG. 6C schematically illustrates, in side view, yet another embodiment of the electrodes 434 and the sensor 466 of the CSF-pulsation detection assembly 460 disposed along the distal end portion 450 of the lead 403. In FIG. 6C, the sensor 466 is shown disposed amongst the electrodes 434 such that the sensor 466 is distal to at least one of the electrodes 434 and proximal to at least one of the electrodes 434.

In at least some embodiments, the CSF-pulsation detection system includes multiple sensors. The CSF-pulsation detection system can include any suitable number of sensors including, for example, one, two, three, four, five, six, seven, eight, nine, ten, twenty, thirty, or more sensors. FIG. 6D schematically illustrates, in side view, another embodiment of the electrodes 434 with multiple sensors 466 of the CSF-pulsation detection assembly 460 disposed along the distal end portion 450 of the lead 403. In FIG. 6D, the CSF detection assembly 460 is shown having two sensors 466a and 466b.

When the CSF-pulsation detection system 450 includes multiple sensors, the multiple sensors can be disposed at any suitable locations along the distal end portion of the lead relative to the electrodes. In at least some embodiments, multiple sensors are disposed distal to the distal-most electrode. In at least some embodiments, multiple sensors are each disposed proximal to the proximal-most electrode. In at least some embodiments, at least one of multiple sensors is disposed between two or more electrodes, while another of the multiple sensors is disposed either proximal or distal to all of the electrodes. In at least some embodiments, each of the multiple sensors is disposed between two or more electrodes. In FIG. 6D, the sensors 466a and 466b are shown flanking each of the electrodes 434, such that the sensor 466a is distal to each of the electrode 434 and the sensor 466b is proximal to each of the electrodes 434.

The sensors shown in FIGS. 4 and 6A-6D are isodiametric with the lead body 406. In at least some embodiments, the one or more sensors have diameters that are different from a diameter of the lead body upon which the one or more sensors are disposed. FIG. 6E schematically illustrates, in side view, yet another embodiment of the electrodes 434 and the sensor 466 of the CSF-pulsation detection assembly 460 disposed along the distal end portion 450 of the lead 403. In FIG. 6E, the sensor 466 is shown having a diameter that is larger than a diameter of the lead body 406.

Figure 7A:
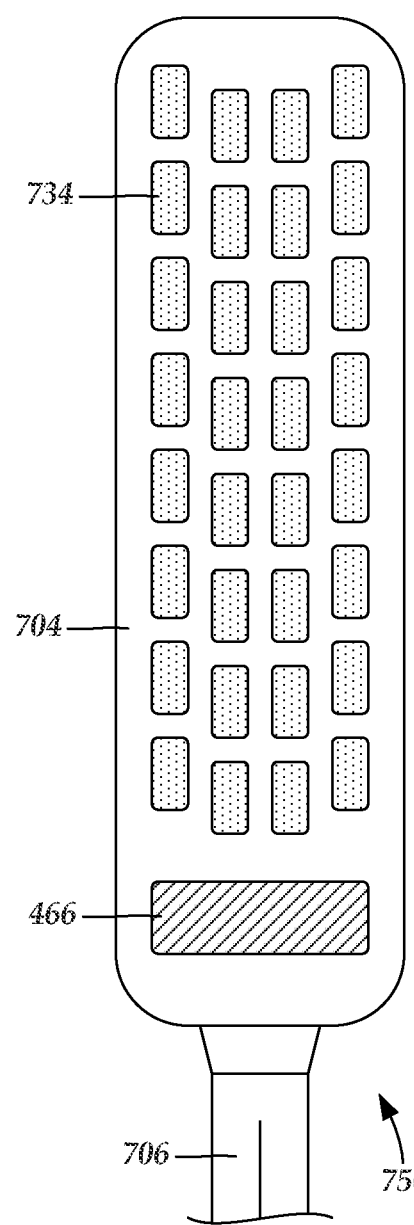
FIG. 7A is a schematic side view of one embodiment of a sensor of the cerebrospinal-fluid-pulsation detection assembly of FIG. 4 disposed along a paddle body disposed along a distal end portion of a lead, the sensor disposed proximal to electrodes also disposed along the paddle body, according to the invention.

In at least some embodiments, the one or more sensors are disposed along a paddle body of a paddle lead. FIG. 7A schematically illustrates, in side view, one embodiment of a paddle lead 703 with a paddle body 704 disposed along a distal end portion 750 of lead bodies 706. Electrodes 734 are disposed along the paddle body 704. The sensor 466 of the CSF-pulsation detection assembly 460 is also disposed along the paddle body 704. In FIG. 7A, the sensor 466 is shown disposed along the paddle body 704 such that the sensor 466 is disposed proximal to the electrodes 734.

Figure 7B:
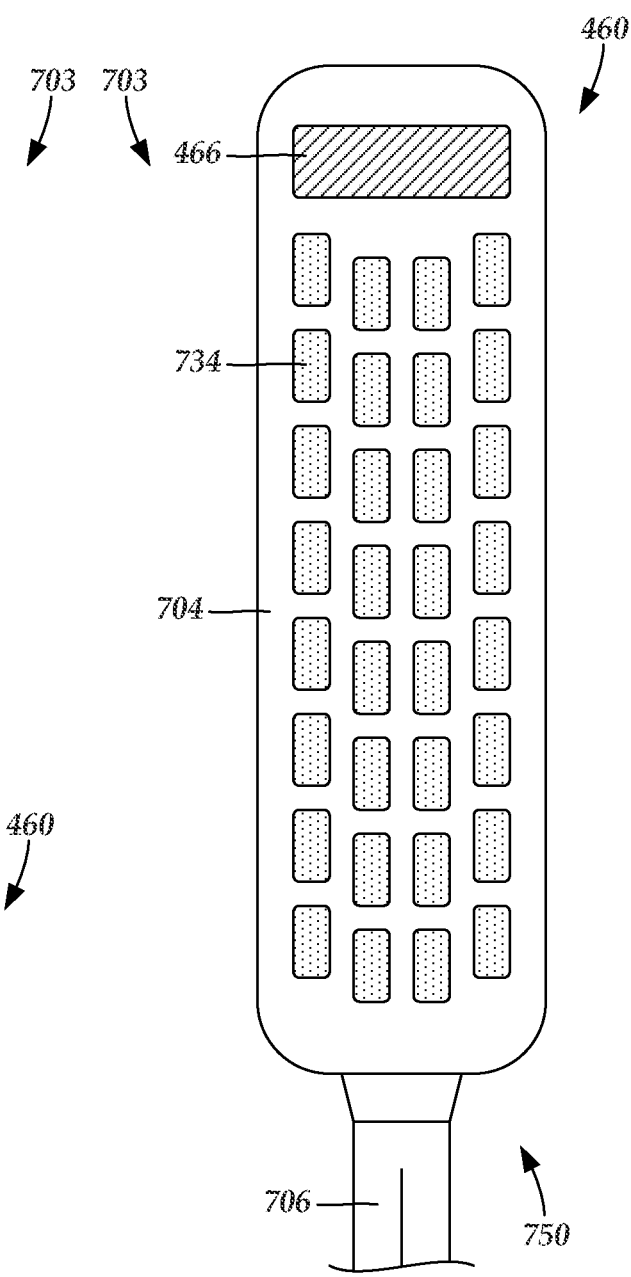
FIG. 7B is a schematic side view of one embodiment of a sensor of the cerebrospinal-fluid-pulsation detection assembly of FIG. 4 disposed along a paddle body of the lead of FIG. 7A, the sensor disposed distal to electrodes also disposed along the paddle body, according to the invention.

FIG. 7B schematically illustrates, in side view, another embodiment of the electrodes 734 and the sensor 466 of the CSF-pulsation detection assembly 460 disposed along the paddle body 704. In FIG. 7B, the sensor 466 is shown disposed distal to the electrodes 734.

Figure 7C:
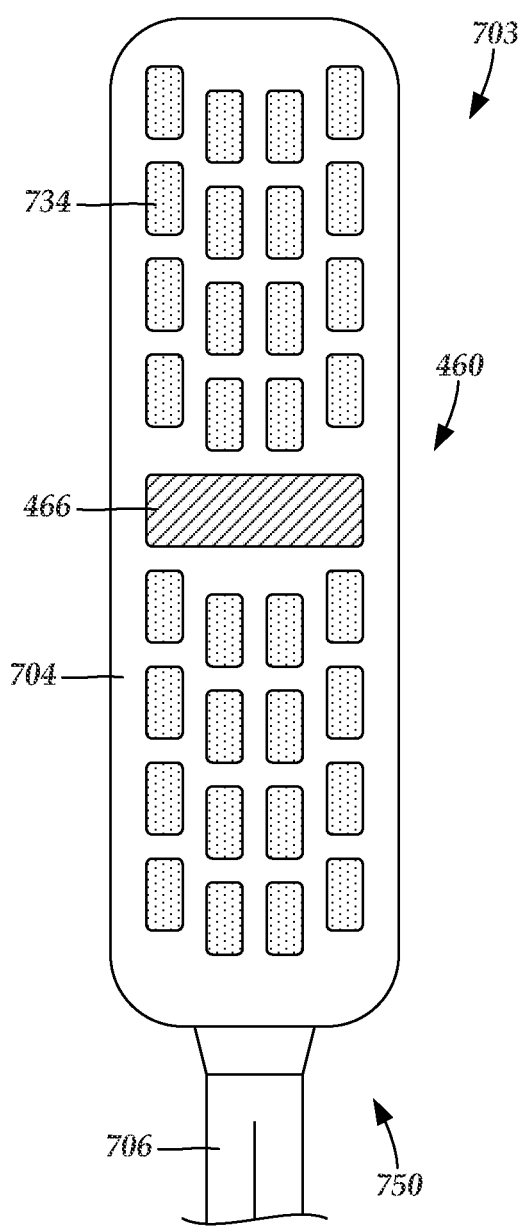
FIG. 7C is a schematic side view of one embodiment of a sensor of the cerebrospinal-fluid-pulsation detection assembly of FIG. 4 disposed along a paddle body of the lead of FIG. 7A such that the sensor is disposed between electrodes axially-spaced apart from one another along the paddle body, according to the invention.

FIG. 7C schematically illustrates, in side view, yet another embodiment of the electrodes 734 and the sensor 466 of the CSF-pulsation detection assembly 460 disposed along the paddle body 704. In FIG. 7C, the sensor 466 is shown disposed between electrodes 734 such that the sensor 466 is disposed proximal to at least one of the electrodes 734 and distal to at least one of the electrodes 734.

Figure 7D:
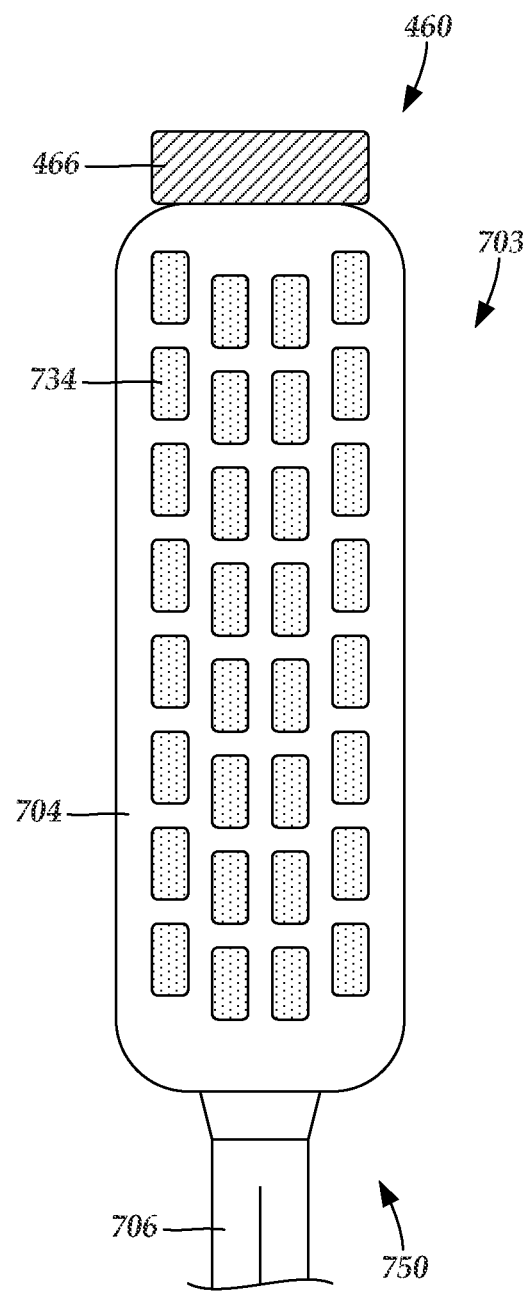
FIG. 7D is a schematic side view of one embodiment of a sensor of the cerebrospinal-fluid-pulsation detection assembly of FIG. 4 disposed along the lead of FIG. 7A with the sensor disposed distal to a paddle body of the lead, according to the invention.

FIG. 7D schematically illustrates, in side view, another embodiment of the electrodes 734 disposed along the paddle body 704. In FIG. 7D, the sensor 466 of the CSF-pulsation detection assembly 460 is shown disposed distal to the paddle body 704. In at least some embodiments, the sensor 466 directly abuts a distal end of the paddle body 704.

Figure 7E:
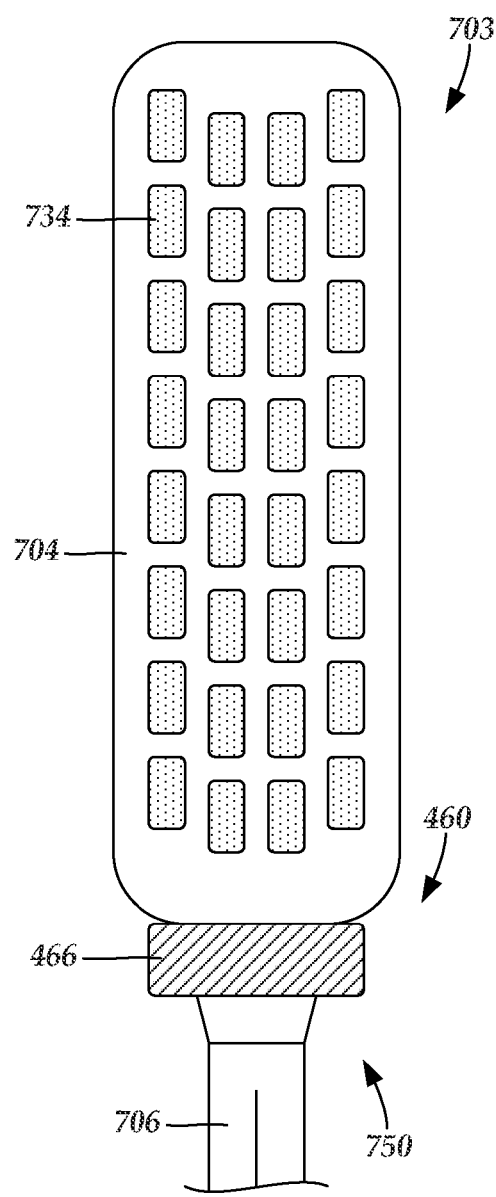
FIG. 7E is a schematic side view of one embodiment of a sensor of the cerebrospinal-fluid-pulsation detection assembly of FIG. 4 disposed along the lead of FIG. 7A with the sensor disposed proximal to a paddle body of the lead, according to the invention.

FIG. 7E schematically illustrates, in side view, another embodiment of the electrodes 734 disposed along the paddle body 704. In FIG. 7D, the sensor 466 of the CSF-pulsation detection assembly 460 is shown disposed proximal to the paddle body 704. In at least some embodiments, the sensor 466 directly abuts a proximal end of the paddle body 704.

Figure 7F:
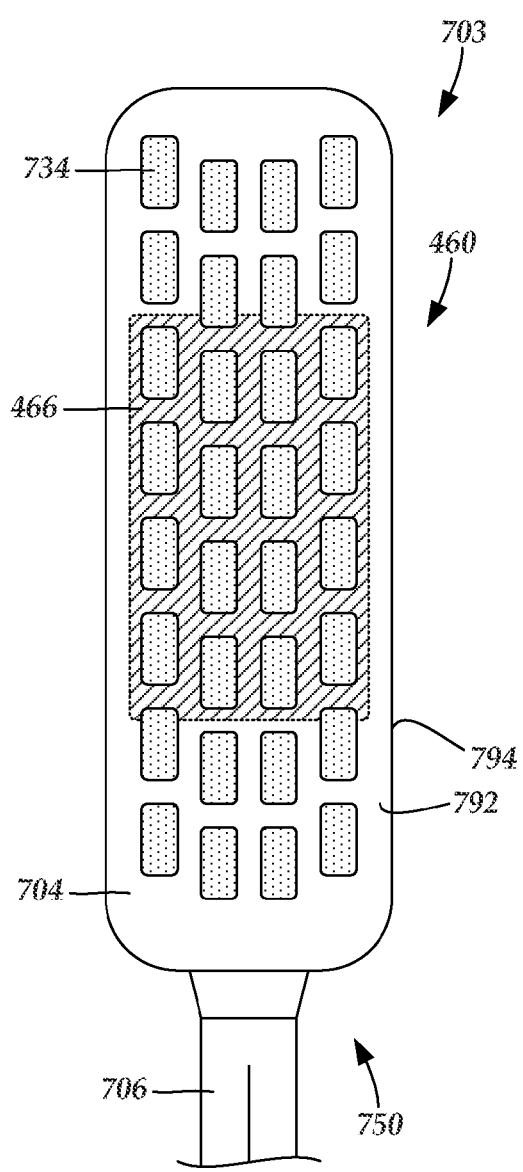
FIG. 7F is a schematic side view of one embodiment of a sensor of the cerebrospinal-fluid-pulsation detection assembly of FIG. 4 disposed along a paddle body of the lead of FIG. 7A such that the sensor is disposed on a surface opposite to a surface along which electrodes are disposed, according to the invention.

FIG. 7F schematically illustrates, in side view, yet another embodiment of the electrodes 734 and the sensor 466 of the CSF-pulsation detection assembly 460 disposed along the paddle body 704. In FIG. 7F, the electrodes 734 are disposed along a first surface 792 of the paddle body, while the sensor 466 of the CSF-pulsation detection assembly 460 is shown disposed along a second surface 794 of the paddle body, opposite to the first surface 792.

Figures 7G, 7H:
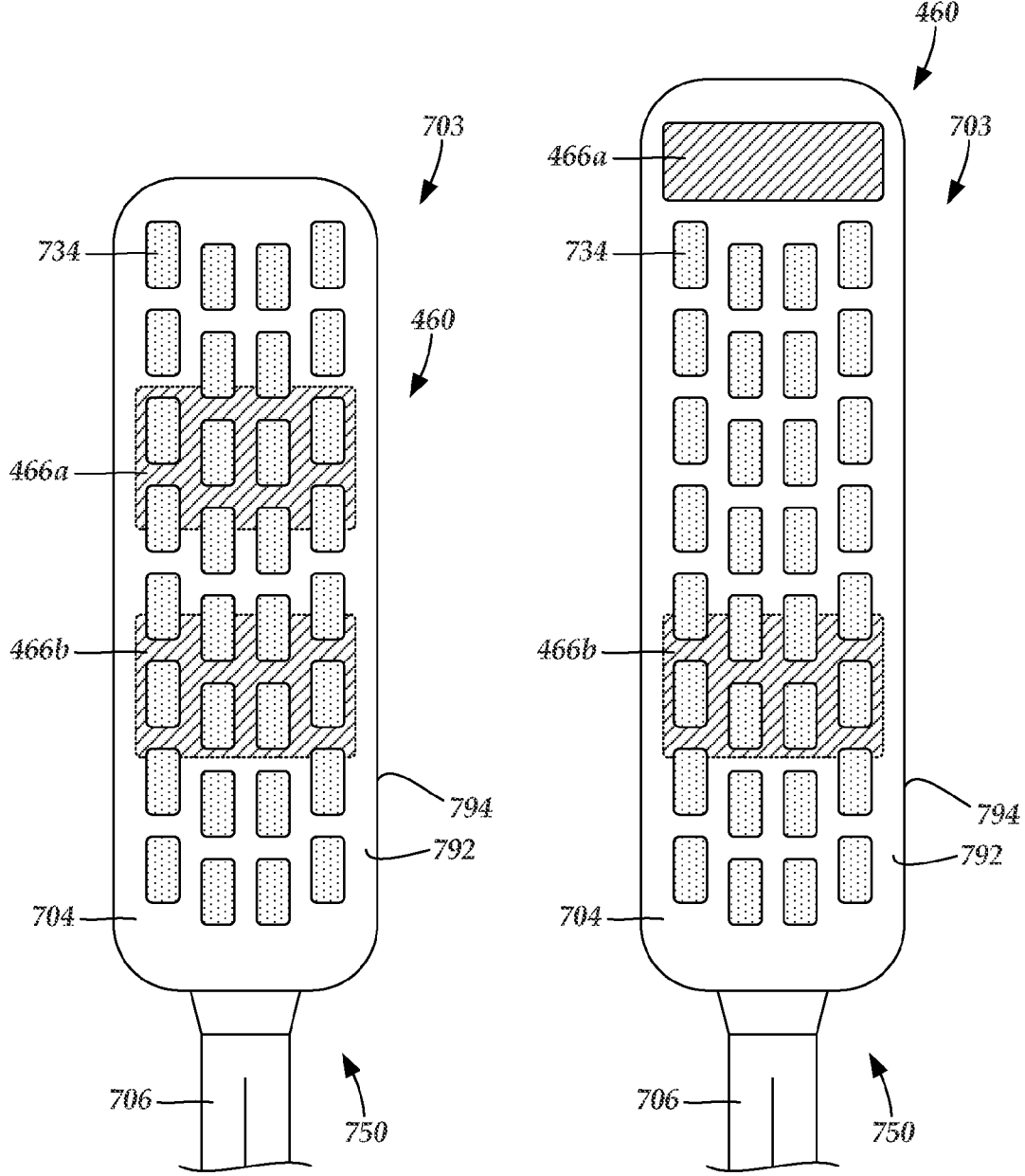
FIG. 7G is a schematic side view of one embodiment of multiple sensors of the cerebrospinal-fluid-pulsation detection assembly of FIG. 4 disposed along a paddle body of the lead of FIG. 7A such that the sensors are disposed on a surface opposite to a surface along which electrodes are disposed, according to the invention.
FIG. 7H is a schematic side view of one embodiment of multiple sensors of the cerebrospinal-fluid-pulsation detection assembly of FIG. 4 disposed along a paddle body of the lead of FIG. 7A such that one of the sensors is disposed on a surface along which electrodes are disposed and another of the sensors is disposed on an opposite surface of the paddle body, according to the invention.

FIG. 7G schematically illustrates, in side view, another embodiment of the electrodes 734 and the sensor 466 of the CSF-pulsation detection assembly 460 disposed along the paddle body 704. In FIG. 7G, the CSF-pulsation detection assembly 460 is shown having two sensors 466a and 466b, with each of the two sensors 466a and 466b disposed along the second surface 794.

FIG. 7H schematically illustrates, in side view, yet another embodiment of the electrodes 734 and the sensor 466 of the CSF-pulsation detection assembly 460 disposed along the paddle body 704. In FIG. 7H, the CSF-pulsation detection assembly 460 is shown having two sensors 466a and 466b, with one of the two sensors 466a disposed along the first surface 792 of the paddle body 704 while the other of the two sensors 466b is disposed along the second surface 794 of the paddle body 704.

In FIG. 7H, the sensor 466a disposed along the first surface 792 is shown disposed distal to the electrodes 734. It will be understood that the sensor 466a disposed along the first surface 792 can be disposed along any suitable portion of the first surface 792 (e.g., distal to at least one of the electrodes, distal to each of the electrodes, proximal to at least one of the electrodes, proximal to each of the electrodes). Similarly, the sensor 466b can be disposed along any suitable portion of the second surface 794.

It will also be understood that other multiple-sensor combinations are possible that include more than two sensors, with any subset of the three or more sensors being disposed along either the first surface 792 or the second surface 794. Additionally, any set of three or more sensors may, optionally, include one or more of the sensors disposed proximal or distal to the paddle body, as shown in FIGS. 7D and 7E. Moreover, it will be understood that, in at least some embodiments, at least one sensor is disposed along one or more other portions of the lead body in addition to, or in lieu of along the distal end portion of the lead 403/703, such as an intermediate portion of the lead, or a proximal end portion of the lead.

Figure 8:
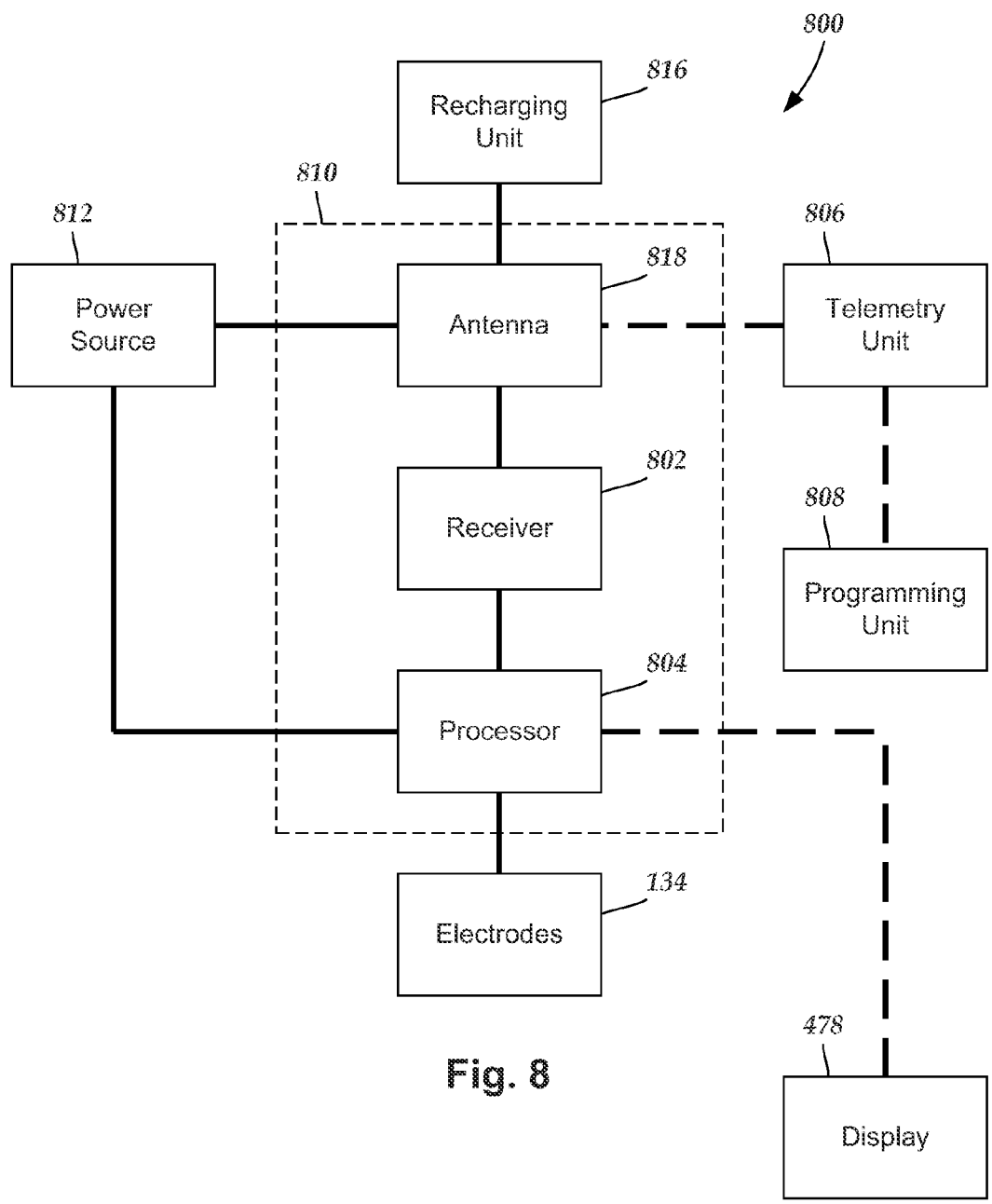
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, a power source 812, an antenna 818, a receiver 802, and a processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 1004 is generally included to control stimulation parameters (e.g., the timing and electrical characteristics) of the electrical stimulation system. For example, the processor 804 can, if desired, control one or more of the timing, frequency, strength, duration, and waveform of the signals. In addition, the processor 804 can select which electrodes can be used to provide stimulation, if desired. In some embodiments, the processor 804 selects which electrode(s) are cathodes and which electrode(s) are anodes. In some embodiments, the processor 804 is used to identify which electrodes provide the most useful stimulation of the desired tissue. Additionally, in at least some embodiments, the processor 804 is used to control operation of the CSF-pulsation detection assembly 460, such as processing signals received from the sensors 466 and estimating patient blood-flow conditions based on the received signals.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by the programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

In at least some embodiments, the CSF-pulsation detection assembly 460 includes the display 478 for displaying, for example, the estimated patient blood-flow condition. The estimated patient blood-flow condition may, optionally, be sent from the processor 804 to the display 478 via the antenna 818.

The signals sent to the processor 804 via the antenna 818 and the receiver 802 can be used to modify or otherwise direct the operation of the electrical stimulation system. For example, the signals may be used to modify the signals of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include the antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the signal parameters so that a user or clinician can determine or verify the characteristics of the signal.

It will be understood that each block of the flowchart illustrations, and combinations of blocks in the flowchart illustrations, as well any portion of the stimulator, CSF-pulsation-detection system, control module, systems and methods disclosed herein, can be implemented by computer program instructions. These program instructions may be provided to a processor to produce a machine, such that the instructions, which execute on the processor, create means for implementing the actions specified in the flowchart block or blocks or described for the sensor, imager, control module, systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead assembly, comprising:
    at least one lead body having a distal end portion, a proximal end portion, and a longitudinal length;
    a plurality of electrodes disposed along the distal end portion of the at least one lead body;
    a plurality of terminals disposed along the proximal end portion of the at least one lead body;
    a plurality of stimulation conductors coupling the plurality of terminals to the plurality of electrodes; and
    a cerebrospinal-fluid-pulsation detection assembly ("CSF-pulsation detection assembly") comprising
        at least one sensor disposed along the distal end portion of the at least one lead body, the at least one sensor configured and arranged for detecting pulses of cerebrospinal fluid within a subarachnoid space of a patient and transforming the detected pulses of cerebrospinal fluid into sensor signals,
        a sensor processor for receiving the sensor signals from the at least one sensor, processing the received sensor signals to generate cerebrospinal-fluid pulsation data ("CSF-pulsation data") comprising at least one of amplitude, duration, or rate of cerebrospinal-fluid pulses, and estimating at least one patient blood-flow condition based on the CSF-pulsation data, and
        at least one sensor control pathway coupling the at least one sensor to the sensor processor.

2. The electrical stimulation lead assembly of claim 1, wherein the at least one sensor of the CSF-pulsation detection assembly comprises at least one of an electro-optical sensor, a photoelectric sensor, a pulse oximeter, a piezoelectric sensor, a pneumatic sensor, or a strain gauge.

3. The electrical stimulation lead assembly of claim 1, wherein the at least one sensor of the CSF-pulsation detection assembly comprises at least one of a light-emitting diode or a laser diode.

4. The electrical stimulation lead assembly of claim 1, wherein the at least one sensor control pathway of the CSF-pulsation detection assembly comprises an optical transport medium.

5. The electrical stimulation lead assembly of claim 1, wherein the at least one sensor is disposed proximal to all of the plurality of electrodes.

6. The electrical stimulation lead assembly of claim 1, wherein the at least one sensor is disposed distal to all of the plurality of electrodes.

7. The electrical stimulation lead assembly of claim 1, further comprising a paddle body disposed along the distal end portion of the at least one lead body, wherein the plurality of electrodes are disposed on the paddle body.

8. The electrical stimulation lead assembly of claim 7, wherein the at least one sensor is disposed on the paddle body.

9. The electrical stimulation lead assembly of claim 1, further comprising a display for displaying the estimated at least one patient blood-flow condition.

10. An electrical stimulating system comprising:
    the electrical stimulation lead assembly of claim 1;
    a control module coupleable to the electrical stimulation lead assembly, the control module comprising
        a housing, and
        an electronic subassembly disposed in the housing; and
    a connector comprising
        a connector housing defining a port configured and arranged for receiving the proximal end portion of the at least one lead body of the electrical stimulation lead assembly, and
        a plurality of connector contacts disposed in the connector housing, the plurality of connector contacts configured and arranged to couple to at least one of the plurality of terminals of the at least one lead body when the proximal end portion of the lead body is received by the port.

11. The electrical stimulation system of claim 10, wherein the sensor processor is disposed in the control module.

12. The electrical stimulation system of claim 10, wherein the sensor processor is disposed external to the patient during operation of the CSF-pulsation detection assembly of the electrical stimulation lead assembly.

13. A method of using an electrical stimulation lead assembly, the method comprising:
    providing the electrical stimulation system of claim 10;
    advancing the electrical stimulation lead assembly of the electrical stimulation system into a patient such that the distal end portion of the at least one lead body of the electrical stimulation lead assembly is in proximity to a target stimulation location along the patient's dura mater;
    stimulating patient tissue by generating electrical stimulation signals in the control module of the electrical stimulation system, propagating the generated electrical stimulation signals to the plurality of electrodes of the electrical stimulation lead assembly, and emitting the electrical stimulation signals from the plurality of electrodes;
    detecting pulses of cerebrospinal fluid within the patient's subarachnoid space using the CSF-pulsation detection assembly of the electrical stimulation lead assembly of the electrical stimulation system;
    transforming the detected pulses of cerebrospinal-fluid into sensor signals; and
    estimating at least one patient blood-flow condition based on the sensor signals.

14. The method of claim 13, wherein estimating the at least one patient blood-flow condition based on the sensor signals comprises estimating at least one of patient heart rate, patient arterial blood flow, or patient venous blood flow.

15. The method of claim 13, wherein estimating at least one patient blood-flow condition comprises
receiving, by the sensor processor of the CSF-pulsation detection assembly, the sensor signals from the at least one sensor of the CSF-pulsation detection assembly;
processing the received sensor signals to generate the CSF-pulsation data; and
estimating the at least one patient blood-flow condition based on the CSF-pulsation data.

16. The method of claim 15, further comprising adjusting the electrical stimulation signals generated in the control module based on the at least one estimated patient blood-flow condition.

17. A non-transitory computer-readable medium having processor-executable instructions for reading data from at least one sensor disposed along a distal end portion of an electrical stimulation lead assembly of an electrical stimulation system, the processor-executable instructions when installed onto a device enable the device to perform actions, comprising:
receiving a sensor signal from the at least one sensor;
processing the received sensor signal to generate cerebrospinal-fluid pulsation data ("CSF-pulsation data") comprising at least one of amplitude, duration, or rate of cerebrospinal-fluid pulses; and
estimating at least one patient blood-flow condition based on the CSF-pulsation data.

18. The computer-readable medium of claim 17, further comprising adjusting electrical stimulation signals generated and emitted by the electrical stimulation system based on the at least one estimated at least one patient blood-flow condition.

19. A lead-based stimulator comprising:
at least one stimulator and at least one sensor disposed along an electrical stimulation lead insertable into a patient, the at least one stimulator configured and arranged for stimulating patient tissue, the at least one stimulator configured and arranged for detecting cerebrospinal-fluid-pulsation, the at least one stimulator and the at least one sensor each coupled to a control module; and
a processor in communication with the control module, the processor for executing processor-readable instructions that enable actions, including:
receiving a sensor signal from the at least one sensor,
processing the received sensor signal to generate cerebrospinal-fluid pulsation data ("CSF-pulsation data") comprising at least one of amplitude, duration, or rate of cerebrospinal-fluid pulses, and
estimating at least one patient blood-flow condition based on the CSF-pulsation data.

20. The lead-based stimulator of claim 19, further comprising adjusting electrical stimulation signals generated and emitted by the stimulator based on the at least one estimated at least one patient blood-flow condition.

* * * * *